United States Patent
Homma et al.

(10) Patent No.: US 10,504,225 B2
(45) Date of Patent: Dec. 10, 2019

(54) IMAGE PROCESSING DEVICE, IMAGE PROCESSING METHOD, AND NON-TRANSITORY COMPUTER-READABLE RECORDING MEDIUM HAVING STORED THEREIN IMAGE PROCESSING PROGRAM

(71) Applicants: TOHOKU UNIVERSITY, Sendai-shi, Miyagi (JP); HIROSAKI UNIVERSITY, Hirosaki-shi, Aomori (JP)

(72) Inventors: Noriyasu Homma, Sendai (JP); Masao Sakai, Sendai (JP); Kei Ichiji, Sendai (JP); Naoki Shibusawa, Sendai (JP); Xiaoyong Zhang, Sendai (JP); Makoto Abe, Sendai (JP); Norihiro Sugita, Sendai (JP); Makoto Yoshizawa, Sendai (JP); Yoshihiro Takai, Hirosaki (JP)

(73) Assignees: TOHOKU UNIVERSITY, Sendai-shi, Miyagi (JP); HIROSAKI UNIVERSITY, Hirosaki-shi, Aomori (JP)

( * ) Notice: Subject to any disclaimer, the term of this patent is extended or adjusted under 35 U.S.C. 154(b) by 223 days.

(21) Appl. No.: 15/720,125

(22) Filed: Sep. 29, 2017

(65) Prior Publication Data
US 2018/0025493 A1 Jan. 25, 2018

Related U.S. Application Data

(63) Continuation of application No. PCT/JP2015/060275, filed on Mar. 31, 2015.

(51) Int. Cl.
*G06K 9/00* (2006.01)
*G06T 7/00* (2017.01)
(Continued)

(52) U.S. Cl.
CPC .............. *G06T 7/0012* (2013.01); *A61B 6/00* (2013.01); *A61B 6/5264* (2013.01); *G06T 5/008* (2013.01);
(Continued)

(58) Field of Classification Search
CPC .......... G08B 13/1961; G08B 13/19608; G08B 13/19606; G06T 7/251; G06T 7/215;
(Continued)

(56) References Cited

U.S. PATENT DOCUMENTS

| 4,538,227 A | 8/1985 | Toraichi et al. |
| 6,999,620 B1 * | 2/2006 | Harville ............. G06K 9/00362 382/103 |

(Continued)

FOREIGN PATENT DOCUMENTS

| JP | 58-130030 A | 8/1983 |
| JP | 2003-579 A | 1/2003 |

(Continued)

OTHER PUBLICATIONS

Paragios, Nikos, and George Tziritas. "Adaptive detection and localization of moving objects in image sequences." Signal Processing: Image Communication 14.4 (1999): 277-296. (Year: 1999).*

(Continued)

*Primary Examiner* — Avinash Yentrapati
(74) *Attorney, Agent, or Firm* — Myers Wolin, LLC.

(57) ABSTRACT

An image processing device includes: an acquisition unit that acquires a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values; a distribution estimation unit that estimates a mixture (Continued)

distribution indicating the acquired probability distribution; a component estimation unit that estimates a component corresponding to a smallest expectation value distribution of which an expectation value is the smallest among a plurality of partial distributions that form the estimated mixture distribution, and forming at least a portion of the luminance of the pixel; a removal unit that removes the estimated component from the luminance of the pixel included in the perspective image.

7 Claims, 15 Drawing Sheets

(51) Int. Cl.
*A61B 6/00* (2006.01)
*G06T 7/194* (2017.01)
*G06T 5/00* (2006.01)
*G06T 7/143* (2017.01)
*G06T 7/11* (2017.01)
*G06T 5/40* (2006.01)

(52) U.S. Cl.
CPC ............... *G06T 5/40* (2013.01); *G06T 7/11* (2017.01); *G06T 7/143* (2017.01); *G06T 7/194* (2017.01); *G06T 2207/10116* (2013.01)

(58) Field of Classification Search
CPC ... G06T 7/10; G06T 7/11; G06T 7/143; G06T 7/149; G06T 7/162; G06T 7/174; G06T 7/136; G06K 9/38; H04N 1/403
See application file for complete search history.

(56) References Cited

U.S. PATENT DOCUMENTS

| | | | |
|---|---|---|---|
| 2003/0053671 A1 | 3/2003 | Dewaele et al. | |
| 2003/0058237 A1* | 3/2003 | Lee ........................ | G06K 9/38 345/418 |
| 2004/0001612 A1* | 1/2004 | Gutta ................. | G06K 9/00771 382/107 |
| 2006/0126933 A1* | 6/2006 | Porikli .................... | G06K 9/38 382/173 |
| 2007/0237393 A1* | 10/2007 | Zhang .................... | G06K 9/38 382/173 |
| 2008/0031493 A1* | 2/2008 | Brogren ............. | G06K 9/00369 382/103 |
| 2009/0226060 A1* | 9/2009 | Gering ..................... | G06T 7/11 382/128 |
| 2010/0111370 A1* | 5/2010 | Black ................. | G06K 9/00369 382/111 |
| 2011/0038536 A1* | 2/2011 | Gong ........................ | G06T 7/11 382/164 |
| 2012/0114226 A1* | 5/2012 | Kameyama ........ | G06K 9/00221 382/155 |
| 2012/0232418 A1* | 9/2012 | Kimura .............. | A61B 5/02411 600/528 |
| 2013/0129255 A1* | 5/2013 | Homma ................. | A61B 6/487 382/294 |
| 2013/0170696 A1* | 7/2013 | Zhu .......................... | G06K 9/68 382/103 |
| 2015/0078640 A1* | 3/2015 | Guo ......................... | G06T 7/11 382/131 |
| 2016/0140724 A1* | 5/2016 | Ji ............................. | G06K 9/62 382/173 |
| 2016/0283784 A1* | 9/2016 | Kounavis ........... | G06K 9/00355 |
| 2017/0372479 A1* | 12/2017 | Somanath ............... | G06T 7/136 |
| 2018/0025493 A1* | 1/2018 | Homma .................. | A61B 6/00 382/132 |
| 2018/0025749 A1* | 1/2018 | Oh ....................... | G06K 9/6218 386/278 |

FOREIGN PATENT DOCUMENTS

| | | |
|---|---|---|
| JP | 2005-65856 A | 3/2005 |
| JP | 2009-192519 A | 8/2009 |
| JP | 2011-78069 A | 4/2011 |
| JP | 2011-512999 A | 4/2011 |

OTHER PUBLICATIONS

Choi, JinMin, Yung Jun Yoo, and Jin Young Choi. "Adaptive shadow estimator for removing shadow of moving object." Computer Vision and Image Understanding 114.9 (2010): 1017-1029. (Year: 2010).*
International Search Report issued for corresponding International Patent Application No. PCT/JP2015/060275, dated Jun. 16, 2015.
Choi et al., "Adaptive Shadow Estimator for Removing Shadow of Moving Object", Computer Vision and Image Understanding 114 (2010) pp. 1017-1029, Available online Jun. 10, 2010.
Calderara et al., "Vision Based Smoke Detection System Using Image Energy and Color Information", Machine Vision and Applications 22 (2011) pp. 705-719, published online May 21, 2010.
International Preliminary Report on Patentability issued for corresponding International Patent Application No. PCT/JP2015/060275, dated Oct. 3, 2017.

* cited by examiner

IMAGE PROCESSING DEVICE, IMAGE PROCESSING METHOD, AND NON-TRANSITORY COMPUTER-READABLE RECORDING MEDIUM HAVING STORED THEREIN IMAGE PROCESSING PROGRAM

CROSS-REFERENCE TO RELATED APPLICATION

This application is a continuation application of International Application PCT/JP2015/060275, filed on Mar. 31, 2015 and designated the U.S., the entire contents of which are incorporated herein by reference.

FIELD OF THE INVENTION

The present invention relates to an image processing device, an image processing method, and a non-transitory computer-readable recording medium having stored therein an image processing program.

BACKGROUND OF THE INVENTION

An image processing device that processes a plurality of non-perspective images captured at a plurality of different time points is known (for example, see Non-Patent Documents 1 and 2). Pixels included in a non-perspective image indicate a foreground or a background. For example, the foreground is a moving object such as a vehicle and the background is a static object such as a building and a road.

This image processing device determines whether a pixel indicates a foreground or a background based on a mixture normal distribution.

Specifically, the image processing device acquires a probability distribution of luminance of a pixel in a plurality of non-perspective images based on an occurrence frequency of a non-perspective image in which the luminance of the pixel has respective values of a plurality of values. In other words, the probability distribution of the luminance of the pixel indicates the percentage of the number of non-perspective images in which the luminance of the pixel has respective values of a plurality of values among the plurality of non-perspective images to the total number of non-perspective images, and the luminance of the pixel is used as a random variable.

Furthermore, the image processing device estimates a mixture normal distribution indicating the acquired probability distribution and determines whether the pixel indicates a foreground or a background based on the estimated mixture normal distribution.

For example, as illustrated in FIG. 1(A), the luminance of a pixel included in an image changes with a change in the time point at which the image was captured. In this case, the probability distribution of the luminance of the pixel is represented as in FIG. 1(B).

However, when a plurality of objects are present on a straight line extending along the direction in which a non-perspective image is captured, a pixel included in the non-perspective image indicates an object positioned on the foremost side. Therefore, when a foreground is a moving object, a period in which the pixel indicates a background may be longer than a period in which the pixel indicates a foreground.

Therefore, when the luminance of the pixel corresponds to a normal distribution G1 having the largest probability among a plurality of normal distributions G1 and G2 that form the estimated mixture normal distribution, the image processing device determines that the pixel indicates a background.

Non-Patent Documents 1: J. Choi, and two others, "Adaptive Shadow Estimator for Removing Shadow of Moving Object," Computer Vision and Image Understanding, Elsevier Inc., 2010, Vol. 114, p. 1017-1029

Non-Patent Documents 2: S. Calderara, and two others, "Vision Based Smoke Detection System Using Image Energy and Color Information," Machine Vision and Applications, Springer, 2010, Vol. 22, p. 705-719

SUMMARY OF THE INVENTION

By processing a perspective image using this image processing device, a target object (for example, a tumor, a soft tissue, an affected region, a diseased tissue, or the like) in the perspective image may be identified. However, when objects are present on a straight line extending along the direction in which the perspective image is captured, the luminance of a pixel included in the perspective image is superposition of luminance components resulting from the respective objects. For example, the superposition of the luminance components resulting from the respective objects is the sum of luminance components resulting from the respective objects.

Due to this, it was difficult to identify a target object in a perspective image with high accuracy even when the perspective image is processed using the above-described image processing device.

One of the objects of the present invention is to provide an image processing device capable of identifying a target object in a perspective image with high accuracy.

According to one aspect, an image processing device includes:

an acquisition unit that acquires a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values;

a distribution estimation unit that estimates a mixture distribution indicating the acquired probability distribution;

a component estimation unit that estimates a component corresponding to a smallest expectation value distribution of which an expectation value is the smallest among a plurality of partial distributions that form the estimated mixture distribution, and forming at least a portion of the luminance of the pixel;

a removal unit that removes the estimated component from the luminance of the pixel included in the perspective image.

According to another aspect, an image processing method includes:

acquiring a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values;

estimating a mixture distribution indicating the acquired probability distribution;

estimating a component corresponding to a smallest expectation value distribution of which an expectation value is the smallest among a plurality of partial distributions that form the estimated mixture distribution, and forming at least a portion of the luminance of the pixel;

removing the estimated component from the luminance of the pixel included in the perspective image.

According to another aspect, a non-transitory computer-readable recording medium having stored therein an image processing program for causing a computer to execute a process includes:

acquiring a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values;

estimating a mixture distribution indicating the acquired probability distribution;

estimating a component corresponding to a smallest expectation value distribution of which an expectation value is the smallest among a plurality of partial distributions that form the estimated mixture distribution, and forming at least a portion of the luminance of the pixel;

removing the estimated component from the luminance of the pixel included in the perspective image.

It is possible to identify a target object in a perspective image with high accuracy.

DESCRIPTION OF EMBODIMENTS

The inventor of the present application found that it is highly probable that a smallest expectation value distribution in which an expectation value is the smallest among a plurality of distributions that forms a mixture distribution indicating a probability distribution of luminance of a pixel included in a perspective image corresponds to an object different from a target object.

Therefore, in each embodiment to be described later, an image processing device estimates a component corresponding to a smallest expectation value distribution and forming at least a portion of luminance of a pixel and removes the estimated component from the luminance of the pixel included in a perspective image.

According to this configuration, it is possible to extract a component resulting from a target object among the luminance components of the pixel included in the perspective image with high accuracy. As a result, it is possible to identify a target object in a perspective image with high accuracy.

Hereinafter, embodiments of an image processing device, an image processing method, and an image processing program according to the present invention will be described with reference to FIGS. 2 to 15.

<First Embodiment>
(Configuration)

Figure 1:
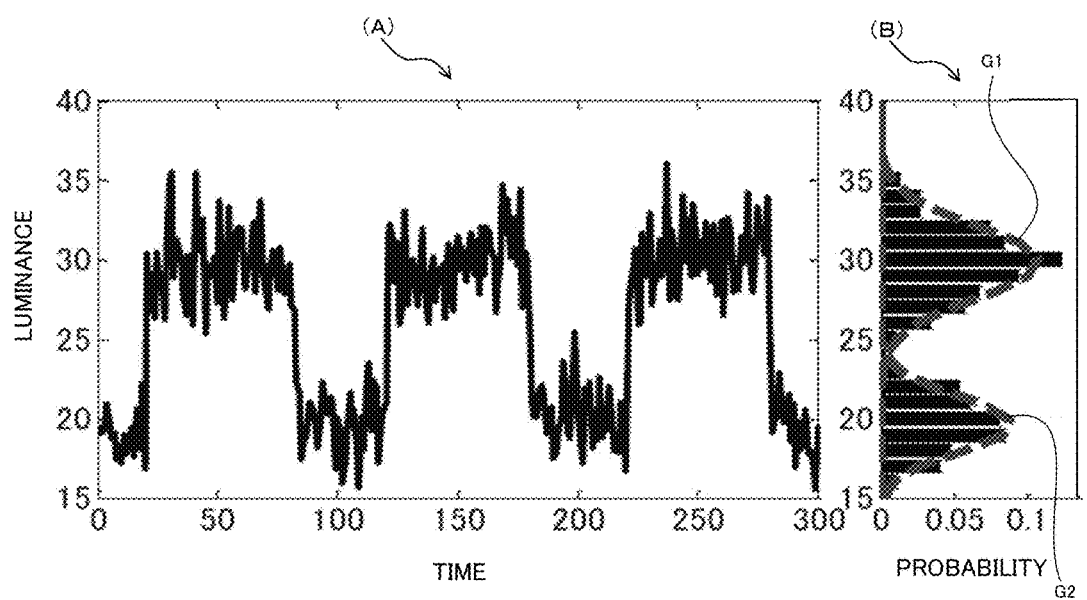
FIG. 1 is a graph illustrating an example of a change over time in luminance and an example of a probability distribution of luminance.
Figure 2:
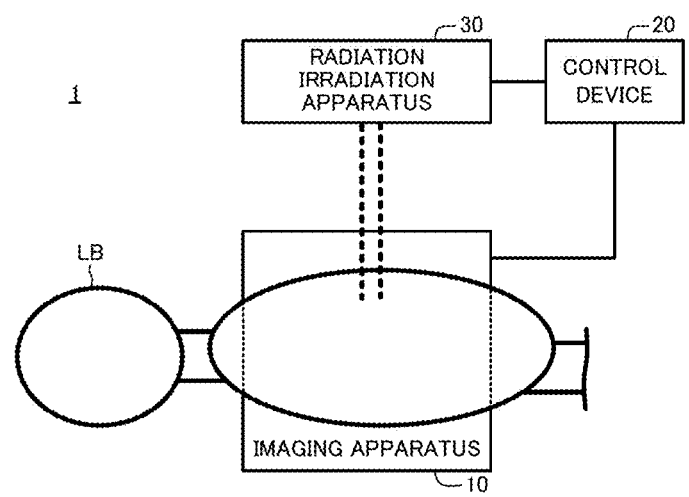
FIG. 2 is a block diagram illustrating an example of a configuration of a radiation irradiation system according to a first embodiment.

As illustrated in FIG. 2, a radiation irradiation system 1 according to a first embodiment includes an imaging apparatus 10, a control device 20, and a radiation irradiation apparatus 30.

The imaging apparatus 10 captures a perspective image of a living body LB whenever a predetermined capturing period has elapsed. In this example, the imaging apparatus 10 captures the perspective image using X-rays. In this example, the lower the transmittance of X-rays to an object, the higher the luminance resulting from the object in the perspective image.

The imaging apparatus 10 outputs the captured perspective image to the control device 20 whenever the perspective image is captured. In this example, the perspective image output to the control device 20 includes the luminance of each of $N_{xmax} N_{ymax}$ pixels arranged in a grid such that $N_{xmax}$ pixels are arranged in an X-axis direction and $N_{ymax}$ pixels are arranged in a Y-axis direction orthogonal to the X-axis direction. $N_{xmax}$ and $N_{ymax}$ indicate a natural number.

The control device 20 receives a plurality of perspective images captured at a plurality of different time points having a time interval corresponding to the capturing period from the imaging apparatus 10. The perspective image input to the control device 20 is also referred to as an input perspective image. The control device 20 processes a plurality of input perspective images and estimates the position of a target object in the living body LB based on the processed perspective images. For example, the target object is a tumor, a soft tissue, an affected region, a diseased tissue, or the like. The target object may be also referred to as a specific object.

Processing on the plurality of input perspective images will be described later.

The control device 20 controls irradiation of radiation to the living body LB by the radiation irradiation apparatus 30 based on the estimated position of the target object.

In this example, the control device 20 controls a period in which the living body LB is irradiated with radiation based on the estimated position of the target object. The control device 20 may control the intensity of radiation irradiating the living body LB based on the estimated position of the target object. Moreover, the control device 20 may control the position irradiated with radiation based on the estimated position of the target object.

The radiation irradiation apparatus 30 irradiates the living body LB with radiation according to the control of the control device 20.

Here, the control device 20 will be described.

Figure 3:
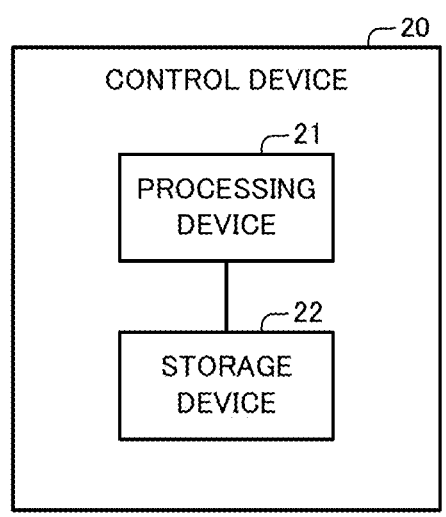
FIG. 3 is a block diagram illustrating an example of a configuration of a control device illustrated in FIG. 2.

As illustrated in FIG. 3, the control device 20 includes a processing device 21 and a storage device 22.

The processing device 21 realizes the functions to be described later by executing a program stored in the storage device 22. In this example, the processing device 21 is a central processing unit (CPU). The processing device 21 may be configured as a digital signal processor (DSP) or a programmable logic device (PLD).

The storage device 22 stores information in a readable and writable manner. For example, the storage device 22 includes at least one of a random access memory (RAM), a read only memory (ROM), a hard disk drive (HDD), a solid state disk (SSD), a semiconductor memory, and an organic memory. The storage device 22 may include a recording medium such as a flexible disk, an optical disc, an opto-magnetic disc, and a semiconductor memory and a reading device capable of reading information from the recording medium.

The control device 20 may be realized as an integrated circuit (for example, LSI (large scale integration) or the like).

The control device 20 is an example of the image processing device.

Figure 4:
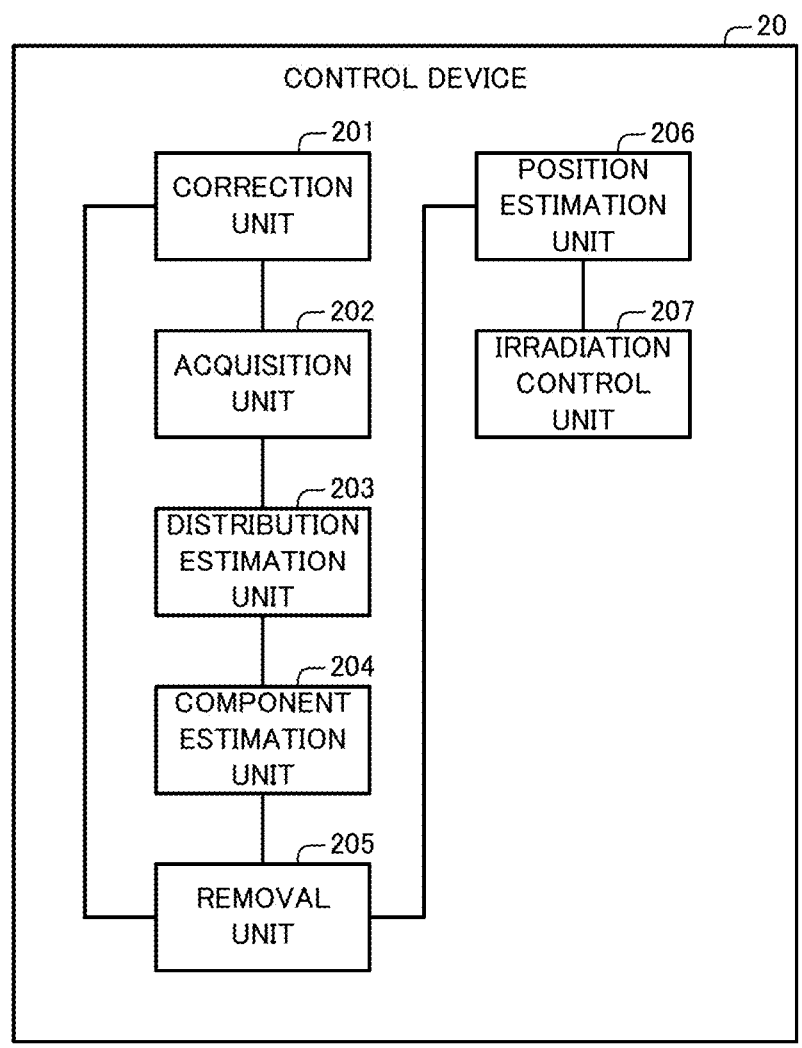
FIG. 4 is a block diagram illustrating an example of a function of the control device illustrated in FIG. 2.

As illustrated in FIG. 4, the function of the control device 20 includes a correction unit 201, an acquisition unit 202, a distribution estimation unit 203, a component estimation unit 204, a removal unit 205, a position estimation unit 206, and an irradiation control unit 207.

In this example, the control device 20 executes a process of removing a removal target component from the luminance of each of a plurality of pixels included in a predetermined target region among the $N_{xmax}N_{ymax}$ pixels included in the perspective image a predetermined number of repetitions M. M indicates a natural number. For example, the removal target component is a component resulting from an object (for example, a bone, a muscle, or the like) different from the target object among the luminance components.

The target object may be a bone, a muscle, or the like. In this case, the object different from the target object may be a soft tissue.

The target region ranges from an $(x_0+1)$th pixel to an $(x_0+N_x)$th pixel in the X-axis direction and ranges from a $(y_0+1)$th pixel to a $(y_0+N_y)$th pixel in the Y-axis direction. $x_0$ and $y_0$ indicate an integer of 1 or more. $N_x$ and $N_y$ indicate an integer of 2 or more. Therefore, the number of pixels included in the target region is $N_xN_y$. In this example, the target region is set by a user of the radiation irradiation system 1. The target region may be changed depending on the number of executions of the removal process. For example, the target region may be changed so as to be narrowed whenever the removal process is executed.

In the first removal process, as illustrated in Equation 1, the control device 20 uses an input perspective image input from the imaging apparatus 10 as a target perspective image of the removal process.

$$I_1(x,y,t)=I_p(x,y,t) \qquad \text{[Math. 1]}$$

$I_m(x,y,t)$ indicates the luminance of a pixel which is an x-th pixel in the X-axis direction and is a y-th pixel in the Y-axis direction among a plurality of pixels included in a t-th perspective image among T target perspective images of an m-th removal process. m indicates integers of 1 to M.

In Equation 1, x indicates integers from 1 to $N_{xmax}$. y indicates integers from 1 to $N_{ymax}$. T indicates an integer of 2 or more. t indicates integers of 1 to T. In this example, a (t+1)th perspective image is a perspective image captured at a time point after a capturing period from a time point at which the t-th perspective image was captured.

$I_p(x,y,t)$ indicates the luminance of a pixel which is an x-th pixel in the X-axis direction and is a y-th pixel in the Y-axis direction among a plurality of pixels included in a t-th input perspective image among T input perspective images.

In this example, in the second and subsequent removal processes, the control device 20 uses a perspective image in which the removal target component is removed in a previous removal process as a target perspective image of the removal process. In at least one removal process of the second and subsequent removal processes, the control device 20 may use a perspective image made up of the removal target component of the previous removal process as the target perspective image of the removal process.

The correction unit 201 selects a reference perspective image among the T target perspective images of the m-th removal process. In this example, the correction unit 201 selects the first perspective image as the reference perspective image. Moreover, the correction unit 201 estimates a moving distance and a moving direction of a subject in each of the T perspective images in relation to the selected reference perspective image. In this example, the subject is represented by a plurality of pixels included in the target region of the first perspective image. The subject may be referred to as a template image.

In this example, the correction unit 201 estimates the moving distance and the moving direction of the subject using a template matching method. The correction unit 201 may use a correlation coefficient as an evaluation function in the template matching method. In this example, the moving distance and the moving direction of the subject are represented by a moving amount $u_m(t)$ in the X-axis direction and a moving amount $v_m(t)$ in the Y-axis direction. $u_m(t)$ and $v_m(t)$ indicate an integer.

The correction unit 201 corrects each of the T perspective images in relation to the position of the subject so that the subject is moved by the estimated moving distance in a direction opposite to the estimated moving direction. In this example, as illustrated in Equation 2, the correction unit 201 corrects the luminance of each of a plurality of pixels included in each of the T perspective images. $I_m'(x,y,t)$ indicates the luminance after correction. Correction of the luminance of a pixel is an example of correction of an image including the pixel.

$$I_m'(x,y,t)=I_m(x-u_m(t),y-v_m(t),t) \qquad \text{[Math. 2]}$$

For example, the moving distance and the moving direction of the subject may be represented by a main moving amount vector based on moving amount vectors of a plurality of pixels included in the target region. For example, a moving amount vector of a pixel indicates a moving distance and a moving direction of the pixel. For example, the main moving amount vector is an average moving amount vector or a most-frequent moving amount vector. The average moving amount vector is obtained by averaging the moving amount vectors of respective pixels of a plurality of pixels included in the target region. The most-frequent moving amount vector is a moving amount vector of which the occurrence frequency is the highest among a plurality of pixels included in the target region.

The acquisition unit 202 acquires a frequency distribution of luminance with respect to each of the plurality of pixels included in the target region based on the luminance $I_m'(x,y,t)$ after correction by the correction unit 201 by counting the number of perspective images in which the luminance of the pixel has respective values among a plurality of values among the T perspective images.

The acquisition unit 202 acquires a probability distribution which uses the luminance of the pixel as a random variable based on the acquired frequency distribution with respect to each of the plurality of pixels included in the target region. In this example, the probability distribution indicates the percentage of the number of perspective images in which the luminance of the pixel has the respective values among a plurality of values among the T perspective images with respect to the total number T of perspective images.

Figure 5:
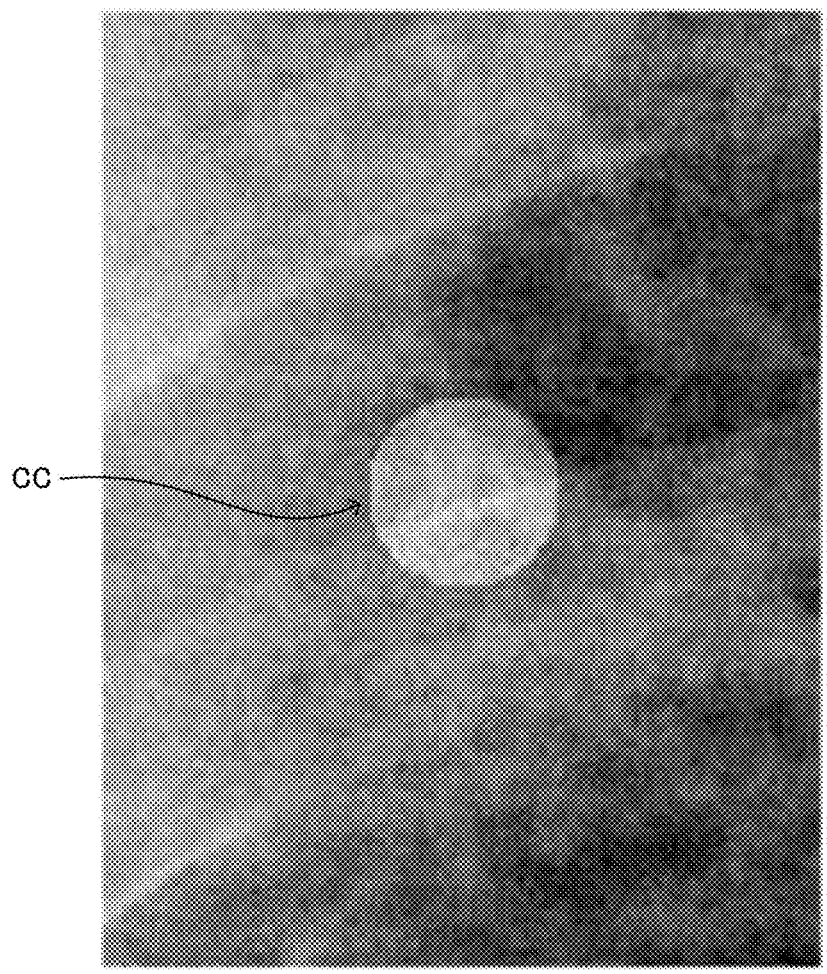
FIG. 5 is a diagram illustrating an example of a perspective image input to the control device illustrated in FIG. 2.
Figure 6:
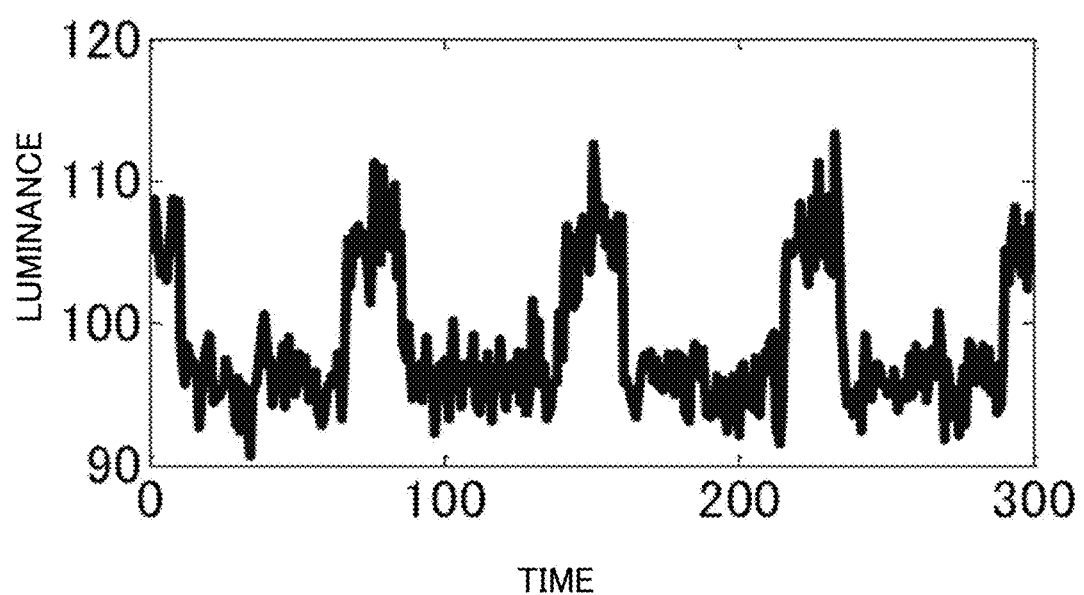
FIG. 6 is a graph illustrating an example of a change over time in luminance.
Figure 7:
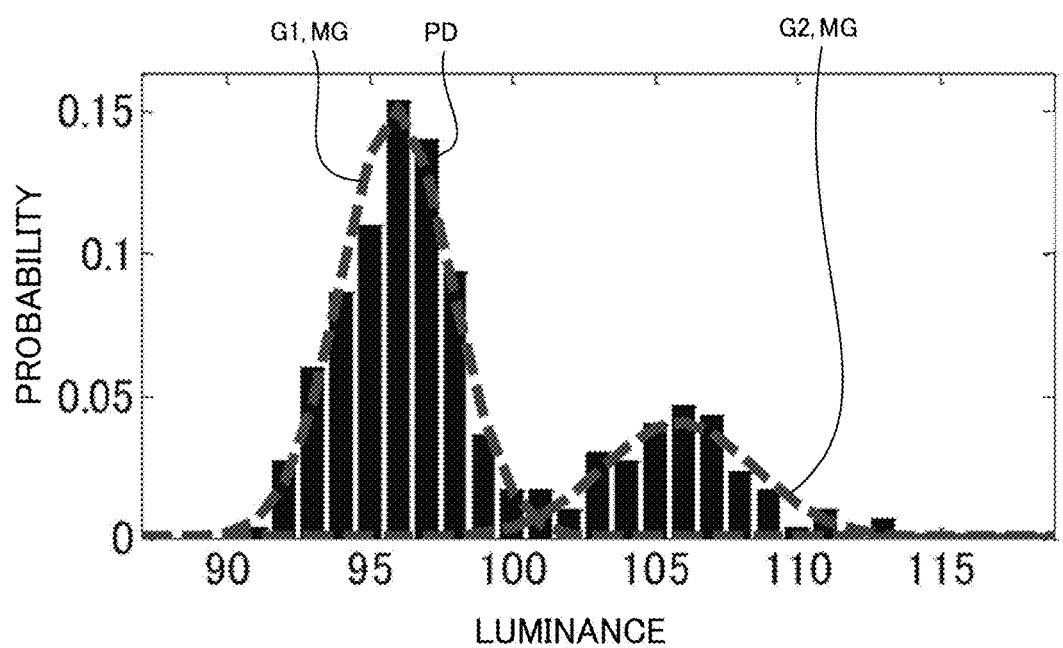
FIG. 7 is a graph illustrating an example of a probability distribution of luminance.

FIG. 5 illustrates an example of a perspective image. A case in which the position of a portion CC which is positioned at the center of a perspective image and has a circular form and which has a higher luminance than other portions changes between perspective images will be considered. Furthermore, a case in which the luminance of a certain pixel changes with time as illustrated in FIG. 6 will be considered. In this case, the acquisition unit 202 acquires a probability distribution PD as illustrated in FIG. 7.

The distribution estimation unit 203 estimates a mixture distribution $p(i_m(x,y))$ indicating the probability distribution acquired by the acquisition unit 202 with respect to each of the plurality of pixels included in the target region. The mixture distribution may be referred to as a mixture probability distribution. In this example, the distribution estimation unit 203 estimates such a mixture normal distribution as illustrated in Equation 3 according to an expectation maximization (EM) algorithm. The mixture normal distribution is an example of a mixture distribution.

$$p(i_m(x,y)) = \Sigma_{j=1}^{J(x,y)} \pi_j(x,y) N(i_m(x,y)|\mu_j(x,y)), \sigma_j^2(x,y))$$ [Math. 3]

$i_m(x,y)$ is a random variable indicating the luminance of a pixel which is the x-th pixel in the X-axis direction and is the y-th pixel in the Y-axis direction. In Equation 3, x indicates integers ranging from $x_0+1$ to $x_0+N_x$. y indicates integers ranging from $y_0+1$ to $y_0+N_y$.

$N(i|\mu,\sigma^2)$ indicates a normal distribution of which the expectation value is $\mu$, the variance is $\sigma^2$, and the random variable is i. The expectation value may be referred to as an average value. The normal distribution is an example of a partial distribution. A distribution different from the normal distribution may be used as the partial distribution. $J(x,y)$ indicates the number of partial distributions that form the mixture distribution of the luminance of a pixel which is the x-th pixel in the X-axis direction and is the y-th pixel in the Y-axis direction. j indicates integers ranging from 1 to $J(x,y)$. $\pi_j(x,y)$ indicates a mixture coefficient of the j-th partial distribution among the $J(x,y)$ partial distributions that form the mixture distribution. $\mu_j(x,y)$ indicates an expectation value of the j-th partial distribution among the $J(x,y)$ partial distributions that form the mixture distribution. $\sigma_j^2(x,y)$ indicates the variance of the j-th partial distribution among the $J(x,y)$ partial distributions that form the mixture distribution.

As illustrated in FIG. 7, when the acquisition unit 202 acquires the probability distribution PD, the distribution estimation unit 203 estimates a mixture distribution MG made up of two partial distributions G1 and G2.

As illustrated in Equation 4, the component estimation unit 204 determines a smallest expectation value distribution of which the expectation value is the smallest among the $J(x,y)$ partial distributions that form the mixture distribution estimated by the distribution estimation unit 203 with respect to each of the plurality of pixels included in the target region.

$$\theta(x,y) = \text{argmin}_{\{j|j=1,\ldots,J(x,y)\}} \mu_j(x,y)$$ [Math. 4]

$\theta(x,y)$ indicates that a $\theta(x,y)$ partial distribution among the $J(x,y)$ partial distributions that form the mixture distribution of the luminance of a pixel which is the x-th pixel in the X-axis direction and is the y-th pixel in the Y-axis direction is the smallest expectation value distribution. $\theta(x,y)$ may be referred to as an index of the smallest expectation value distribution. In Equation 4, x indicates integers ranging from $x_0+1$ to $x_0+N_x$. y indicates integers ranging from $y_0+1$ to $y_0+N_y$.

Furthermore, the component estimation unit 204 estimates a component corresponding to the determined smallest expectation value distribution and forming at least a portion of the luminance of the pixel with respect to each of the plurality of pixels included in the target region of each of the T perspective images. The component corresponding to the smallest expectation value distribution of the luminance of the pixel and forming at least a portion of the luminance of the pixel may be referred to as a removal target component.

In this example, the component estimation unit 204 estimates the removal target component as below.

First, the component estimation unit 204 calculates a probability that the luminance of the pixel results from each of the $J(x,y)$ partial distributions that form the mixture distribution of the luminance of the pixel with respect to each of the plurality of pixels included in the target region of each of the T perspective images based on the luminance $I_m'(x,y,t)$ after correction by the correction unit 201.

In this example, the component estimation unit 204 uses a burden rate $\gamma_k(x,y,t)$ illustrated in Equation 5 as the probability. In Equation 5, x indicates integers ranging from $x_0+1$ to $x_0+N_x$. y indicates integers ranging from $y_0+1$ to $y_0+N_y$.

$$\gamma_k(x,y,t) \equiv p(z_k = 1 | I_m'(x,y,t)) = \frac{\pi_k(x,y) N(I_{m'}(x,y,t) | \mu_k(x,y), \sigma_k^2(x,y))}{\sum_{j=1}^{J(x,y)} \pi_j(x,y) N(I_{m'}(x,y,t) | \mu_j(x,y), \sigma_j^2(x,y))}$$ [Math. 5]

The burden rate $\gamma_k(x,y,t)$ is a probability that the luminance of a pixel of the t-th perspective image, the pixel being the x-th pixel in the X-axis direction and being the y-th pixel in the Y-axis direction, results from a k-th partial distribution under a condition that the luminance of the pixel is $I_m'(x,y,t)$. k indicates integers ranging from 1 to $J(x,y)$.

$z_k$ is a two-valued random variable having a value of 0 or 1. $z_k$ having the value of 1 indicates that the luminance results from the k-th partial distribution. $\{z_1, \ldots, z_{J(x,y)}\}$ is a $J(x,y)$-dimensional vector that follows the 1-of-$J(x,y)$ expression. In other words, any one of $z_1, \ldots, z_{J(x,y)}$ has the value of 1 and the others have the value of 0.

As illustrated in Equation 6, when each of the burden rates $\gamma_j(x,y,t)$ of partial distributions different from the smallest expectation value distribution among the $J(x,y)$ partial distributions that form the mixture distribution of the luminance of each of the plurality of pixels included in the target region of each of the T perspective images is smaller than the burden rate $\gamma_{\theta(x,y)}(x,y,t)$ of the smallest expectation value distribution, the component estimation unit 204 estimates the luminance $I_m'(x,y,t)$ of the pixel as a removal target component $\rho(x,y,t)$. Here, j indicates integers different from $\theta(x,y)$ among the integers ranging from 1 to J(x,y).

$\rho(x,y,t)=I_m'(x,y,t)$ where $\forall\{j|j=1,\ldots,J(x,y) \text{ and } j\neq\theta\},\gamma_{\theta(x,y)}(x,y,t)>\gamma_j(x,y,t)$ [Math. 6]

As illustrated in Equation 7, when at least one of the burden rates $\gamma_j(x,y,t)$ of partial distributions different from the smallest expectation value distribution among the J(x,y) partial distributions that form the mixture distribution of the luminance of each of the plurality of pixels included in the target region of each of the T perspective images is equal to or larger than the burden rate $\gamma_{\theta(x,y)}(x,y,t)$ of the smallest expectation value distribution, the component estimation unit 204 estimates the expectation value $\mu_{\theta(x,y)}(x,y)$ of the smallest expectation value distribution as a removal target component $\rho(x,y,t)$. Here, j indicates integers different from $\theta(x,y)$ among the integers ranging from 1 to J(x,y).

$\rho(x,y,t)=\mu_{\theta(x,y)}(x,y)$ where $\exists\{j|j=1,\ldots,J(x,y) \text{ and } j\neq\theta\},\gamma_{\theta(x,y)}(x,y,t)\leq\gamma_j(x,y,t)$ [Math. 7]

The expectation value $\mu_{\theta(x,y)}(x,y)$ of the smallest expectation value distribution is an example of a value based on the smallest expectation value distribution.

In this case, the component estimation unit 204 may estimate the value determined based on the expectation value $\mu_{\theta(x,y)}(x,y)$ and the variance $\sigma_{\theta(x,y)}^2(x,y)$ of the smallest expectation value distribution instead of the expectation value $\mu_{\theta(x,y)}(x,y)$ of the smallest expectation value distribution as the removal target component $\rho(x,y,t)$.

In this way, the component estimation unit 204 estimates the removal target component.

Figure 8:
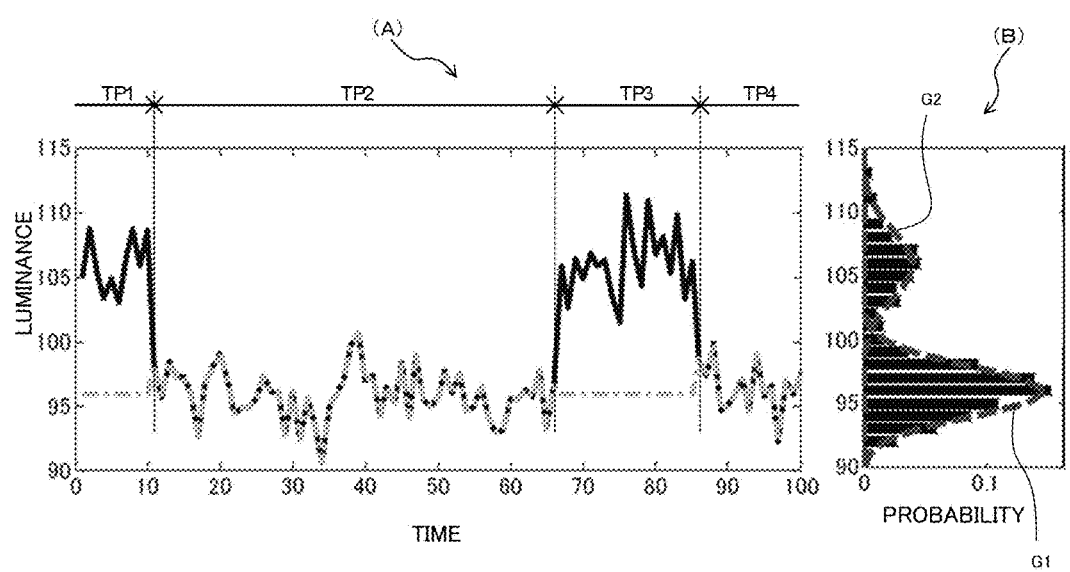
FIG. 8 is a graph illustrating an example of a change over time in a removal target component to be estimated.
Figure 9:
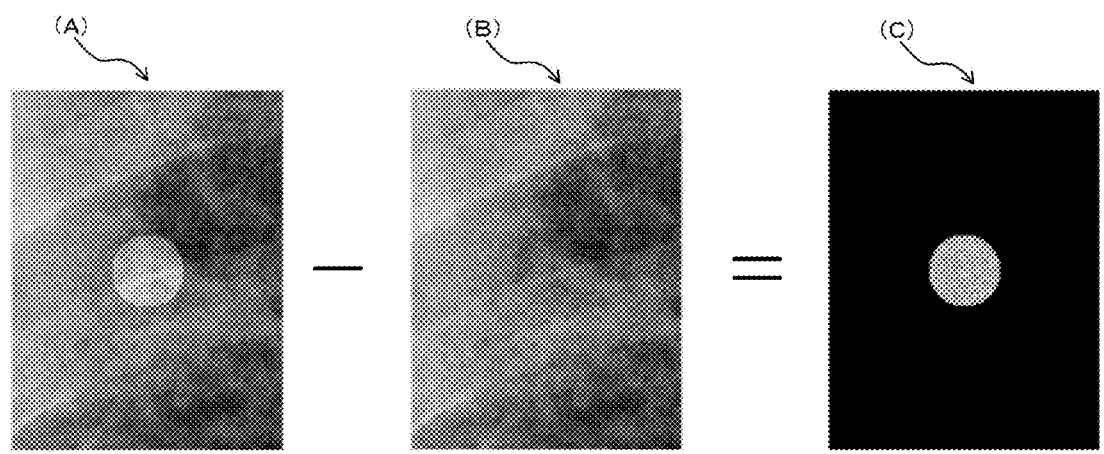
FIG. 9 is an explanatory diagram illustrating an example of removal of a removal target component from an input perspective image.

As illustrated in FIG. 7, when the distribution estimation unit 203 estimates the mixture distribution MG made up of two partial distributions G1 and G2, the component estimation unit 204 determines the partial distribution G1 as the smallest expectation value distribution. Furthermore, in this case, as illustrated in FIG. 8, the component estimation unit 204 estimates the expectation value $\mu_{\theta(x,y)}(x,y)$ of the smallest expectation value distribution as the removal target component $\rho(x,y,t)$ in periods T1 and T3. Moreover, in this case, the component estimation unit 204 estimates the luminance $I_m'(x,y,t)$ as the removal target component $\rho(x,y,t)$ in periods T2 and T4.

The removal unit 205 removes the removal target component $\rho(x,y,t)$ estimated by the component estimation unit 204 from the luminance $I_m'(x,y,t)$ of each of the plurality of pixels included in the target region of each of the T perspective images.

In this example, as illustrated in Equation 8, the removal unit 205 subtracts the removal target component $\rho(x,y,t)$ estimated by the component estimation unit 204 from the luminance $I_m'(x,y,t)$ of each of the plurality of pixels included in the target region of each of the T perspective images. $I_m'(x,y,t)$ indicates the luminance after subtraction.

$I_m''(x,y,t)=I_m'(x,y,t)-\rho(x,y,t)$ [Math. 8]

Furthermore, in this example, the removal unit 205 sets the luminance $I_m''(x,y,t)$ after subtraction as the luminance $I_{m+1}(x,y,t)$ of the target perspective image of the (m+1)th removal process. When m is 2 or more, the removal unit 205 may set the removal target component $\rho(x,y,t)$ estimated by the component estimation unit 204 as the luminance $I_{m+1}(x,y,t)$ of the target perspective image of the (m+1)th removal process.

In this example, the removal unit 205 outputs T perspective images in which the removal target component is removed by M removal processes to the position estimation unit 206. When M is 2 or more, the removal unit 205 may output the perspective image made up of the removal target component $\rho(x,y,t)$ in the M-th removal process to the position estimation unit 206.

In this way, the removal process is executed by the correction unit 201, the acquisition unit 202, the distribution estimation unit 203, the component estimation unit 204, and the removal unit 205.

FIG. 9(A) illustrates an example of a target perspective image of the removal process. FIG. 9(B) illustrates an example of a removal target component as a luminance component resulting from an object different from a target object. FIG. 9(C) illustrates an example of a perspective image in which a removal target component is removed by a removal process. In this case, as illustrated in FIG. 9(C), according to the perspective image in which a removal target component is removed, it is possible to identify a target object with high accuracy. Moreover, when the removal target component is a luminance component resulting from the target object, it is possible to identify the target object with high accuracy using the perspective image made up of the removal target component instead of the perspective image in which the removal target component is removed.

The position estimation unit 206 receives T perspective images in which the removal target component is removed by M removal processes from the removal unit 205. When M is 2 or more, the position estimation unit 206 may receive the perspective image made up of the removal target component $\rho(x,y,t)$ in the M-th removal process from the removal unit 205.

The position estimation unit 206 estimates the position of the target object in the living body LB based on the T perspective images input from the removal unit 205. For example, the position estimation unit 206 estimates the position of the target object using a template matching method.

The irradiation control unit 207 controls irradiation of radiation to the living body LB by the radiation irradiation apparatus 30 based on the position of the target object estimated by the position estimation unit 206.

(Operation)

Next, the operation of the radiation irradiation system 1 will be described.

The imaging apparatus 10 captures a perspective image of the living body LB whenever a capturing period has elapsed and outputs the captured perspective image to the control device 20 whenever the perspective image is captured.

The control device 20 processes a plurality of input perspective images input from the imaging apparatus 10. In this example, the control device 20 executes the process illustrated by the flowchart in FIG. 10 whenever a predetermined execution period has elapsed.

Figure 10:
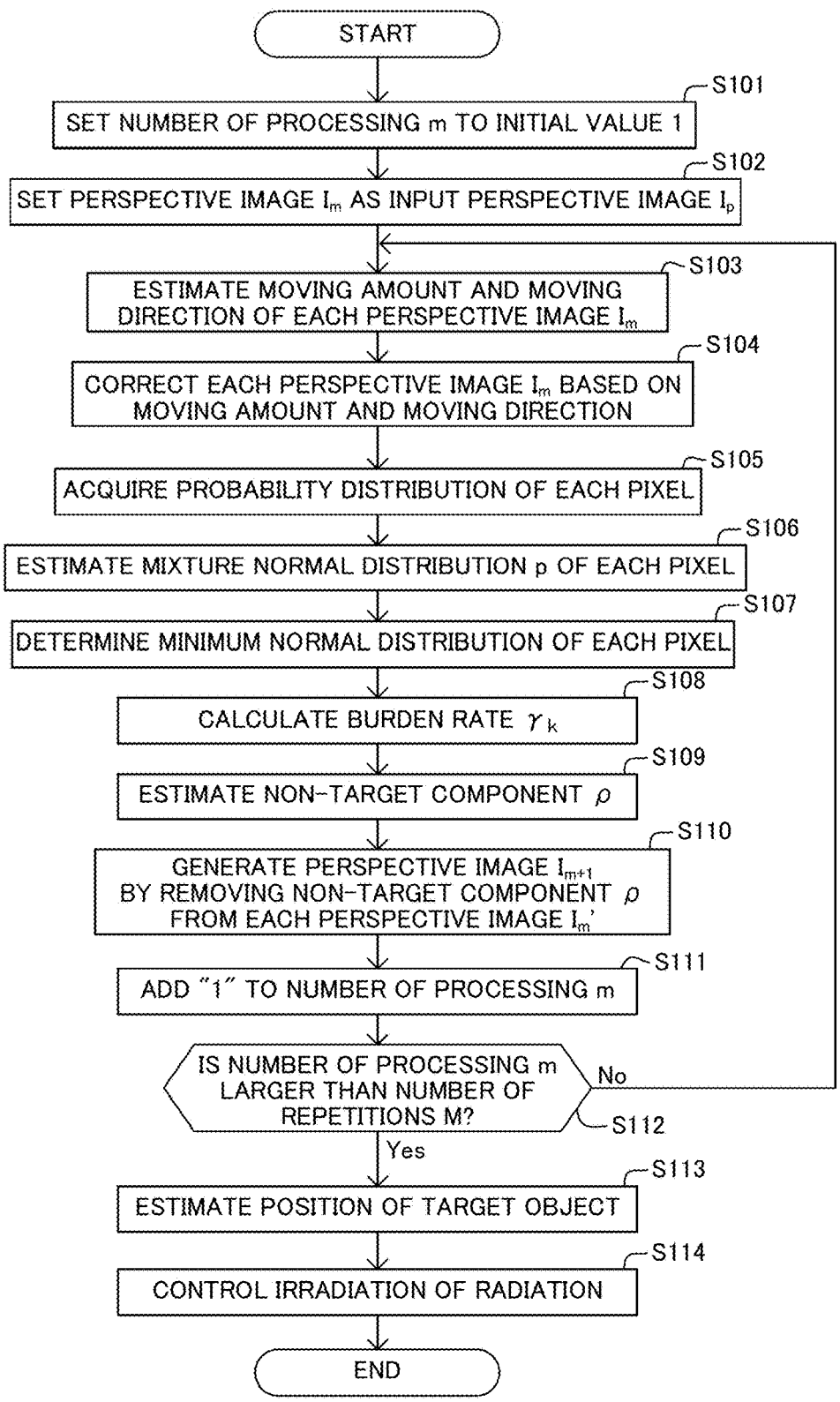
FIG. 10 is a flowchart illustrating an example of a process executed by the control device illustrated in FIG. 2.

Specifically, the control device 20 sets the number of processing m to an initial value "1" (step S101 in FIG. 10). Subsequently, the control device 20 sets the luminance $I_m(x,y,t)$ of a pixel included in a target perspective image of an m-th removal process as the luminance $I_p(x,y,t)$ of the pixel included in the input perspective image (step S102 in FIG. 10).

Subsequently, the control device 20 estimates a moving distance and a moving direction of a subject in each of T perspective images in relation to a reference perspective image selected among the T perspective images (step S103 in FIG. 10). Moreover, the control device 20 corrects each of the T perspective images so that the subject is moved by the estimated moving distance in the direction opposite to the estimated moving direction (step S104 in FIG. 10).

Subsequently, the control device 20 acquires a probability distribution which uses the luminance of each of the plurality of pixels included in a target region as a random variable based on the luminance $I_m'(x,y,t)$ corrected in step S104 (step S105 in FIG. 10).

The control device 20 estimates a mixture distribution $p(i_m(x,y))$ indicating the probability distribution acquired in step S105 with respect to each of the plurality of pixels included in the target region (step S106 in FIG. 10).

Subsequently, the control device 20 determines a smallest expectation value distribution of which the expectation value is the smallest among the $J(x,y)$ partial distributions that form the mixture distribution estimated in step S106 with respect to each of the plurality of pixels included in the target region (step S107 in FIG. 10).

The control device 20 calculates a burden rate $\gamma_k(x,y,t)$ indicating a probability that the luminance $I_m'(x,y,t)$ of each of the plurality of pixels included in the target region of each of the T perspective images results from each of the $J(x,y)$ partial distributions that form the mixture distribution of the luminance of the pixel (step S108 in FIG. 10).

Subsequently, the control device 20 estimates a removal target component $\rho(x,y,t)$ for each of the plurality of pixels included in the target region of each of the T perspective images (step S109 in FIG. 10).

In this example, when the burden rate $\gamma_{\theta(x,y)}(x,y,t)$ of the smallest expectation value distribution is larger than a burden rate $\gamma_j(x,y,t)$ of the partial distribution different from the smallest expectation value distribution, the control device 20 estimates the luminance $I_m'(x,y,t)$ of the pixel as the removal target component $\rho(x,y,t)$.

Furthermore, in this example, when the burden rate $\gamma_{\theta(x,y)}(x,y,t)$ of the smallest expectation value distribution is equal to or smaller than a burden rate $\gamma_j(x,y,t)$ of the partial distribution different from the smallest expectation value distribution, the control device 20 estimates the expectation value $\mu_{\theta(x,y)}(x,y)$ of the smallest expectation value distribution as the removal target component $\rho(x,y,t)$.

Subsequently, the control device 20 sets the luminance $I_{m+1}(x,y,t)$ of the pixel included in the target perspective image of the (m+1)th removal process by removing the removal target component $\rho(x,y,t)$ estimated in step S109 from the luminance $I_m'(x,y,t)$ of each of the plurality of pixels included in the target region of each of the T perspective images (step S110 in FIG. 10). Setting of the luminance of a pixel included in a perspective image may be referred to as generation of a perspective image.

The control device 20 adds "1" to the number of processing m (step S111 in FIG. 10). Subsequently, the control device 20 determines whether the number of processing m is larger than the number of repetitions M (step S112 in FIG. 10).

When the number of processing m is equal to or smaller than the number of repetitions M, the control device 20 determines as "No" and returns to step S103 and repeatedly executes the processes of steps S103 to S112 until the number of processing m becomes larger than the number of repetitions M.

When the number of processing m is larger than the number of repetitions M, the control device 20 determines as "Yes" in step S112 and proceeds to step S113. Moreover, the control device 20 estimates the position of the target object based on the perspective image in which the removal target component $\rho(x,y,t)$ estimated in the previous removal process is removed (step S113 in FIG. 10). The control device 20 may estimate the position of the target object based on the perspective image made up of the removal target component $\rho(x,y,t)$ estimated in the previous removal process.

Subsequently, the control device 20 controls irradiation of radiation by the radiation irradiation apparatus 30 based on the position of the target object estimated in step S113 (step S114 in FIG. 10).

After that, the control device 20 ends the process of FIG. 10.

As described above, the control device 20 of the first embodiment estimates the mixture distribution indicating the probability distribution of the luminance of each pixel. Furthermore, the control device 20 estimates a component corresponding to the smallest expectation value distribution of which the expectation value is the smallest among the plurality of partial distributions that forms the estimated mixture distribution, and forming at least a portion of the luminance of the pixel. Furthermore, the control device 20 removes the estimated component from the luminance of the pixel included in the perspective image.

According to this configuration, it is possible to extract a component resulting from the target object among the luminance components of the pixel included in the perspective image with high accuracy. As a result, it is possible to identify the target object in the perspective image with high accuracy.

Furthermore, when a probability that the luminance of a pixel results from the smallest expectation value distribution is higher than a probability that the luminance of the pixel results from a partial distribution different from the smallest expectation value distribution among the plurality of partial distributions that forms the estimated mixture distribution, the control device 20 of the first embodiment estimates the luminance of the pixel as the component.

When a probability that the luminance of a pixel results from the smallest expectation value distribution is higher than a probability that the luminance of the pixel results from a partial distribution different from the smallest expectation value distribution among the plurality of partial distributions that forms the mixture distribution, it is highly probable that the luminance of the pixel has a component resulting from an object corresponding to the smallest expectation value distribution only.

In this case, the control device 20 estimates the luminance of the pixel as a component corresponding to the smallest expectation value distribution. In this way, it is possible to remove a component resulting from an object corresponding to the smallest expectation value distribution from the luminance components of the pixel included in the perspective image with high accuracy. As a result, it is possible to identify the target object in the perspective image with high accuracy.

Furthermore, when a probability that the luminance of a pixel results from the smallest expectation value distribution is lower than a probability that the luminance of the pixel results from a partial distribution different from the smallest expectation value distribution among the plurality of partial distributions that forms the estimated mixture distribution, the control device 20 of the first embodiment estimates a value based on the smallest expectation value distribution as the component.

When a probability that the luminance of a pixel results from the smallest expectation value distribution is lower than a probability that the luminance of the pixel results from a partial distribution different from the smallest expectation value distribution among the plurality of partial distributions that forms the mixture distribution, it is highly probable that the luminance of the pixel includes components resulting from other objects in addition to the component resulting from the object corresponding to the smallest expectation value distribution.

In this case, the control device 20 estimates a value (for example, the expectation value of the smallest expectation value distribution) based on the smallest expectation value distribution as the component corresponding to the smallest expectation value distribution. In this way, it is possible to remove the component resulting from the object corresponding to the smallest expectation value distribution appropriately from the luminance of the pixel included in the perspective image. As a result, it is possible to identify the target object in the perspective image with high accuracy.

Furthermore, the control device 20 of the first embodiment executes removal of the component with respect to each of the plurality of perspective images. In addition, the control device 20 repeatedly executes acquisition of the probability distribution, estimation of the mixture distribution, estimation of the component, and removal of the component with respect to the plurality of perspective images in which the component is removed.

In this way, when the luminance of the pixel includes a component resulting from each of a plurality of objects different from the target object, it is possible to extract the component resulting from the target object among the luminance components of the pixel included in the perspective image with high accuracy. As a result, it is possible to identify the target object in the perspective image with high accuracy.

Furthermore, the control device 20 of the first embodiment estimates the moving distance and the moving direction of the object in each of the plurality of perspective images in relation to the reference perspective image selected among a plurality of perspective images. In addition, the control device 20 corrects each of the plurality of perspective images so that the subject is moved by the estimated moving distance in the direction opposite to the estimated moving direction.

In this way, it is possible to suppress the influence of the movement of the subject on the luminance of the pixel included in the perspective image. As a result, it is possible to extract a component resulting from the target object among the luminance components of the pixel included in the perspective image with high accuracy. As a result, it is possible to identify the target object in the perspective image with high accuracy.

Next, the processing result by the control device 20 of the first embodiment, on a simulated perspective image that simulates a clinical perspective image will be described.

Figure 11:
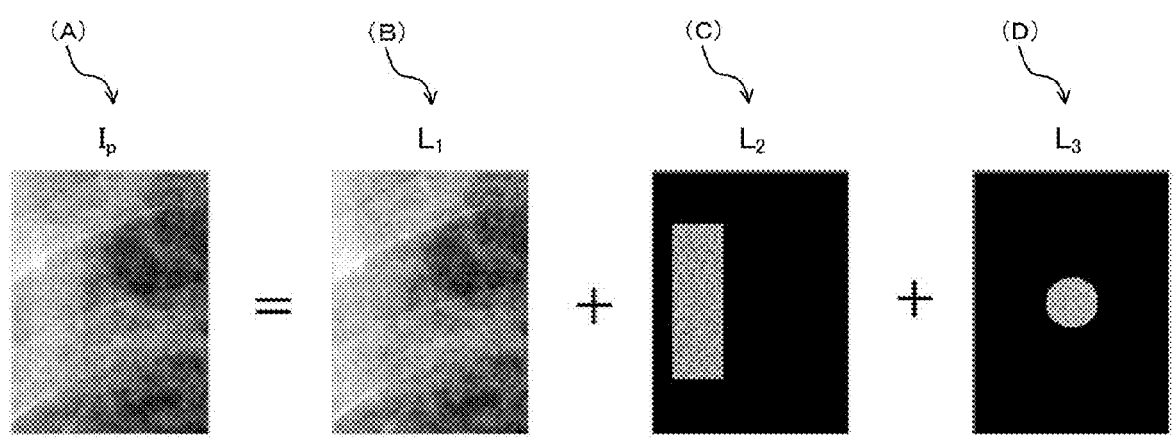
FIG. 11 is an explanatory diagram illustrating an example of a simulated perspective image.
Figure 12:
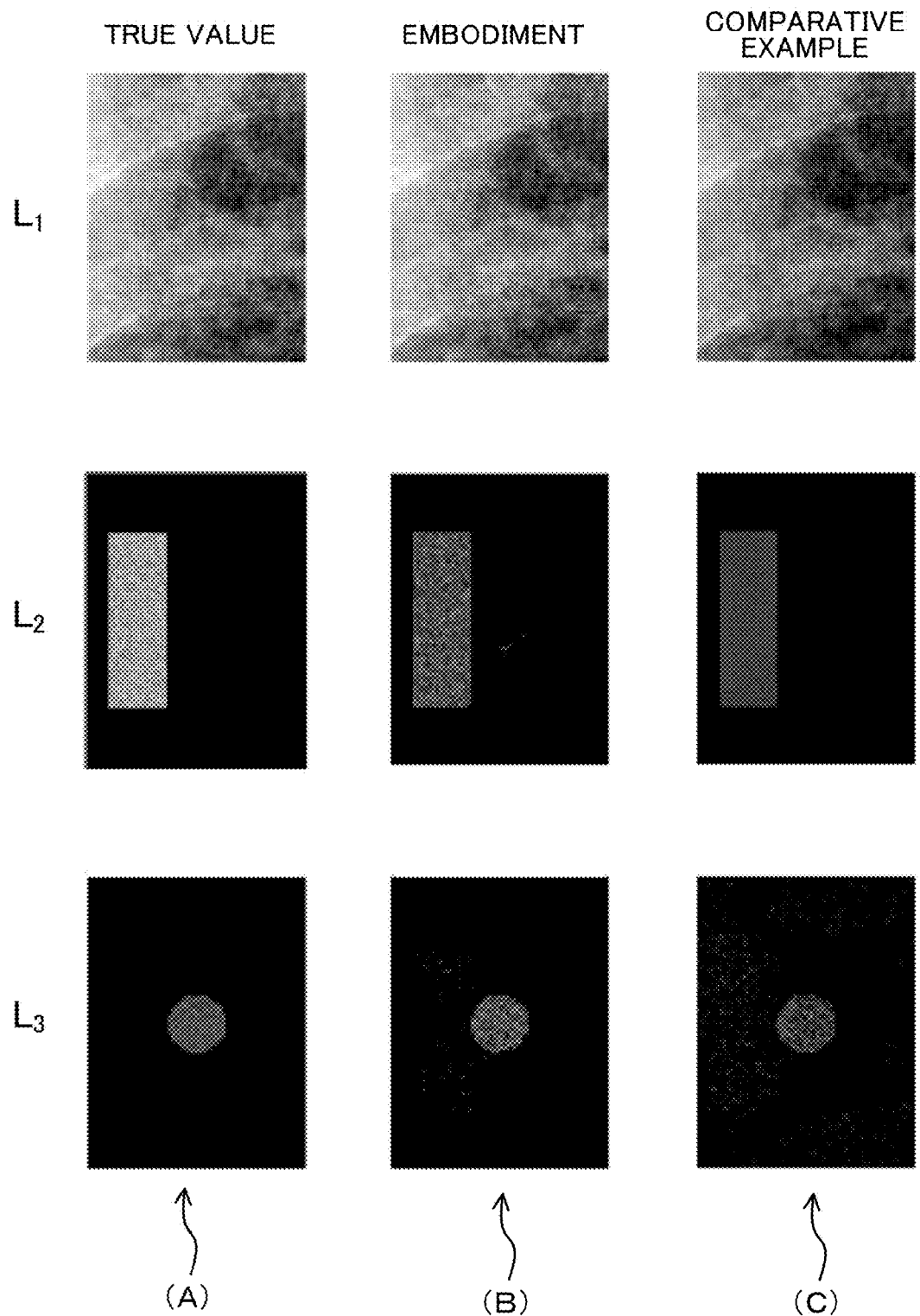
FIG. 12 is a diagram illustrating an example of the result of removal of a removal target component from a simulated perspective image.

As illustrated in FIG. 11, a simulated perspective image is an image obtained by superposing first to third base images. FIG. 11(A) illustrates a simulated perspective image. FIGS. 11(B) to 11(D) illustrate first to third base images, respectively. In this example, as illustrated in Equation 9, the luminance of each pixel of the image obtained by superposing a plurality of base images is the sum of the luminance components of the pixels of the plurality of base images.

$$I_p(x,y,t) = \sum_{j=1}^{J} L_j(x,y,t)$$ [Math. 9]

$I_p(x,y,t)$ indicates the luminance of the pixel included in the simulated perspective image. $L_j(x,y,t)$ indicates the luminance of the pixel included in the j-th base image. J indicates 3. j indicates integers ranging from 1 to J.

The first base image is an image obtained by adding Gauss noise of which the expectation value is 0 and the variance is 4 to the clinical perspective image.

The second base image is an image obtained by adding Gauss noise of which the expectation value is 15 and the variance is 4 to a rectangle.

The third base image is an image obtained by adding Gauss noise of which the expectation value is 10 and the variance is 1 to a circle that simulates a tumor.

The rectangle in the second base image moves in the X-axis direction with time so that the position in the X-axis direction of the rectangle changes along a sinusoidal wave.

The circle in the third base image moves in the Y-axis direction with time so that the position in the Y-axis direction of the circle changes along a sinusoidal wave.

FIG. 12(A) illustrates the true value of each base image. FIG. 12(B) illustrates the processing result by the control device 20 of the first embodiment. FIG. 12(C) illustrates the processing result by an image processing device of a comparative example. The image processing device of the comparative example uses an intrinsic image deriving method (DII: Deriving Intrinsic Image) disclosed in Non-Patent Document (Y. Weiss, "Deriving Intrinsic Images from Image Sequences", International Conference on Computer Vision, 2001, Vol. 2, p. 68-75).

The drawing at the top of FIG. 12(B) illustrates a removal target component estimated in the first removal process. The drawing in the middle of FIG. 12(B) illustrates a removal target component estimated in the second removal process. The drawing at the bottom of FIG. 12(B) illustrates a perspective image in which the removal target component is removed in the second removal process.

Figure 13:
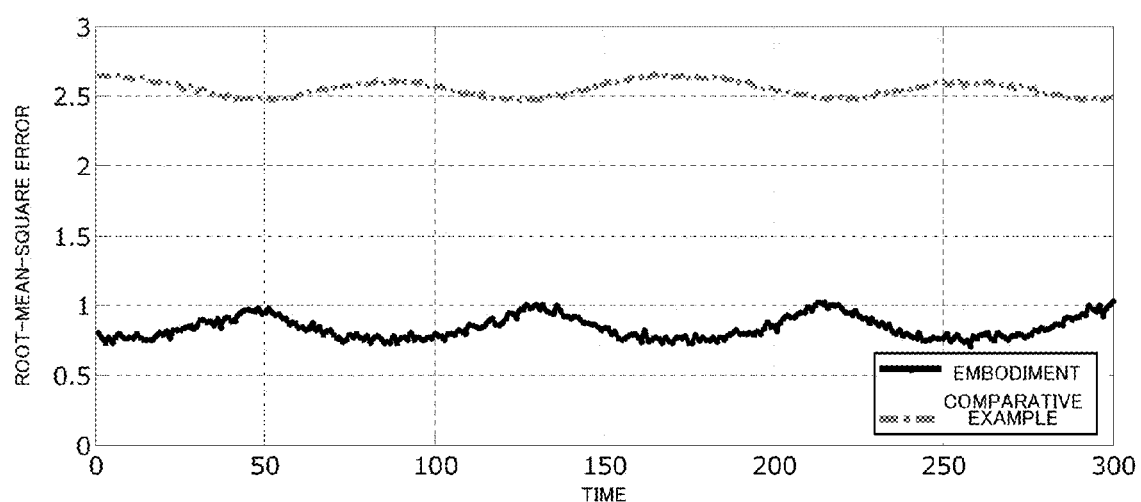
FIG. 13 is a graph illustrating an example of a change over time in a root-mean-square error with respect to the luminance of each pixel of a simulated perspective image.

A root-mean-square error $L_{rmse}$ of the luminance of a pixel included in the perspective image in which the removal target component is removed in the second removal process by the control device 20 of the first embodiment with respect to the luminance of a pixel included in the third base image is represented by Equation 10. FIG. 13 illustrates a change over time in the root-mean-square error $L_{rmse}$. The root-mean-square error $L_{rmse}$ of the control device 20 of the first embodiment is smaller than that of the image processing device of the comparative example.

$$L_{rmse} = \sqrt{\frac{1}{N_x N_y} \sum_{x=1}^{N_x} \sum_{y=1}^{N_y} \{L_3(x,y,t) - I_3(x,y,t)\}^2}$$ [Math. 10]

In this manner, according to the control device 20 of the first embodiment, it is possible to extract a component resulting from the target object among the luminance components of the pixel included in the perspective image with high accuracy. As a result, it is possible to identify the target object in the perspective image with high accuracy.

Next, the processing result by the control device 20 of the first embodiment, on a clinical perspective image will be described.

Figure 14:
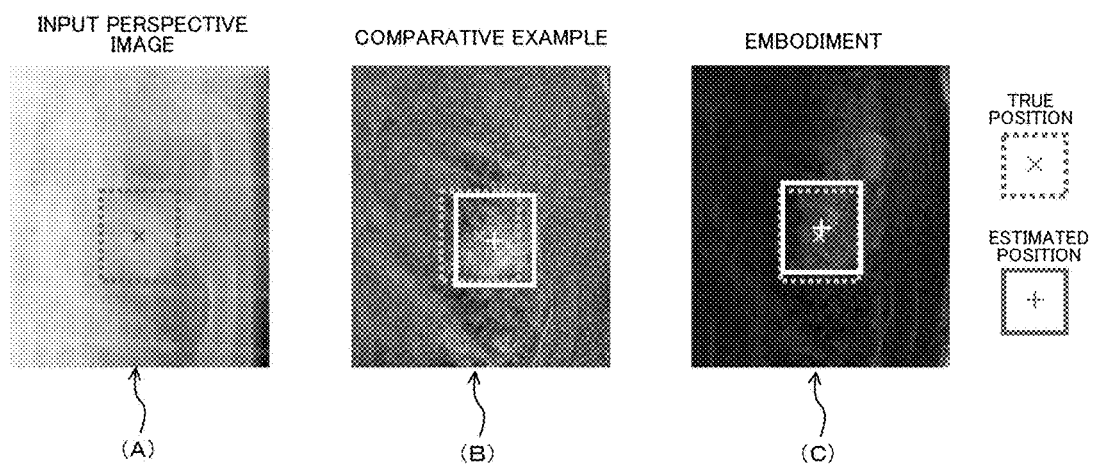
FIG. 14 is a diagram illustrating an example of an estimation result of the position of a target object in relation to a clinical perspective image.

FIG. 14(A) illustrates an input perspective image. FIG. 14(B) illustrates the processing result by the image processing device of the comparative example. FIG. 14(C) illustrates the processing result by the control device 20 of the first embodiment. In FIG. 14, a dotted rectangle indicates the true position of the target object. In FIG. 14(B), a solid rectangle indicates the position of the target object estimated by the image processing device of the comparative example. In FIG. 14(C), a solid rectangle indicates the position of the target object estimated by the control device 20 of the first embodiment.

Figure 15:
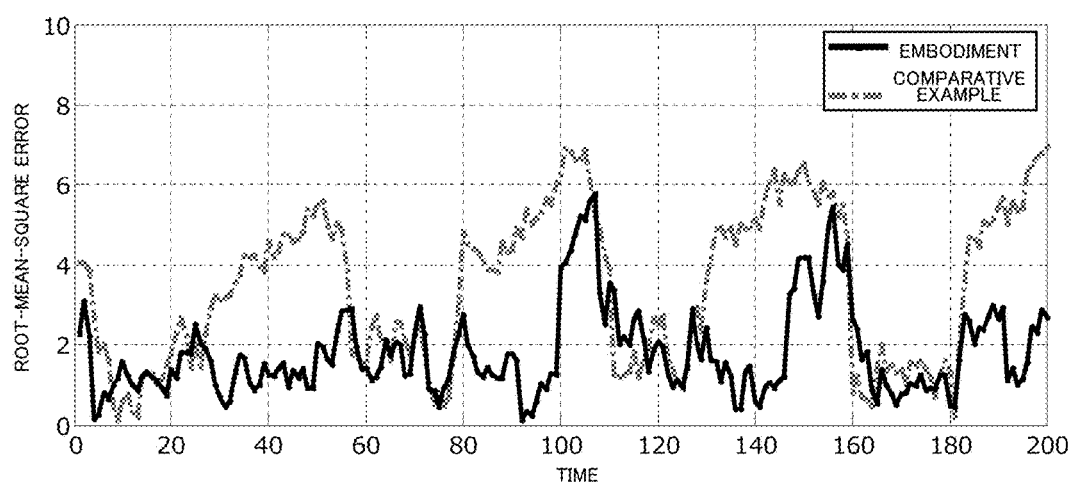
FIG. 15 is a graph illustrating an example of a change over time in a root-mean-square error in relation to the position of a target object of a clinical perspective image.

The root-mean-square error $P_{rmse}$ of the position of the target object estimated by the control device 20 of the first embodiment with respect to the true position of the target object is represented by Equation 11. $\omega_e(t)$ and $\lambda_e(t)$ indicate the estimated positions in the X-axis direction and the Y-axis direction of the target object, respectively. $\omega_0(t)$ and $\lambda_0(t)$ indicate the true positions in the X-axis direction and the Y-axis direction of the target object, respectively. FIG. 15 illustrates a change over time in the root-mean-square error $P_{rmse}$. The root-mean-square error $P_{rmse}$ of the control device 20 of the first embodiment is smaller than that of the image processing device of the comparative example.

$$P_{rmse} = \{\overline{\omega}_e(t) - \overline{\omega}_0(t)\}^2 - \{\lambda_e(t) - \lambda_0(t)\}^2 \quad \text{[Math. 11]}$$

In this manner, according to the control device 20 of the first embodiment, it is possible to estimate the position of the target object in the perspective image with high accuracy.

In the first embodiment, the control device 20 controls the radiation irradiation apparatus 30. However, the control device 20 may be an image processing device that does not control the radiation irradiation apparatus 30. In this case, the control device 20 may output or transmit the perspective image in which the removal target component is removed.

The present invention is not limited to the above-described embodiment. For example, various changes which can be conceived by a person skilled in the art without departing from the spirit of the present invention can be made to the above-described embodiment. For example, an arbitrary combination of the above-described embodiment and modifications may be employed as modifications of the above-described embodiment without departing from the spirit of the present invention.

What is claimed is:

1. An image processing device comprising processor circuitry, the processor circuitry being configured to:
   acquire a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values;
   estimate a mixture distribution indicating the acquired probability distribution;
   estimate a component corresponding to a smallest expectation value distribution of which an expectation value is the smallest among a plurality of partial distributions that form the estimated mixture distribution, and forming at least a portion of the luminance of the pixel;
   remove the estimated component from the luminance of the pixel included in the perspective image.

2. The image processing device according to claim 1, wherein
   processor circuitry estimates the luminance of the pixel as the component when a probability that the luminance of the pixel results from the smallest expectation value distribution is higher than a probability that the luminance of the pixel results from a partial distribution different from the smallest expectation value distribution among the plurality of partial distributions that form the estimated mixture distribution.

3. The image processing device according to claim 1, wherein
   the processor circuitry estimates a value based on the smallest expectation value distribution as the component when a probability that the luminance of the pixel results from the smallest expectation value distribution is lower than a probability that the luminance of the pixel results from a partial distribution different from the smallest expectation value distribution among the plurality of partial distributions that form the estimated mixture distribution.

4. The image processing device according to claim 1, wherein
   the processor circuitry executes removal of the component in each of the plurality of perspective images, and
   the processor circuitry repeatedly executes acquisition of the probability distribution, estimation of the mixture distribution, estimation of the component, and removal of the component with respect to the plurality of perspective images in which the component is removed.

5. The image processing device according to claim 1, wherein
   the processor circuitry estimates a moving distance and a moving direction of a subject in each of the plurality of perspective images in relation to a reference perspective image selected among the plurality of perspective images and corrects the perspective image so that the subject is moved by the estimated moving distance in a direction opposite to the estimated moving direction with respect to each of the plurality of perspective images.

6. An image processing method comprising:
   acquiring a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values;
   estimating a mixture distribution indicating the acquired probability distribution;
   estimating a component corresponding to a smallest expectation value distribution of which an expectation value is the smallest among a plurality of partial distributions that form the estimated mixture distribution, and forming at least a portion of the luminance of the pixel;
   removing the estimated component from the luminance of the pixel included in the perspective image.

7. A non-transitory computer-readable recording medium having stored therein an image processing program for causing a computer to execute a process comprising:
   acquiring a probability distribution of luminance of a pixel in a plurality of perspective images including the luminance of the pixel which is superposition of luminance components resulting from respective objects, based on an occurrence frequency of a perspective image in which the luminance of the pixel has respective values of a plurality of values;
   estimating a mixture distribution indicating the acquired probability distribution;
   estimating a component corresponding to a smallest expectation value distribution of which an expectation value is the smallest among a plurality of partial distributions that form the estimated mixture distribution, and forming at least a portion of the luminance of the pixel;

removing the estimated component from the luminance of the pixel included in the perspective image.

* * * * *